United States Patent [19]

Marshall et al.

[11] Patent Number: 5,611,809
[45] Date of Patent: Mar. 18, 1997

[54] NEEDLE DEVICES FOR MEDICAL USE

[75] Inventors: Jeremy Marshall; Stuart Weekes, both of Oxford, United Kingdom

[73] Assignee: Owen Mumford Limited, Woodstock, United Kingdom

[21] Appl. No.: 563,532

[22] Filed: Nov. 6, 1995

[30] Foreign Application Priority Data

Nov. 4, 1994 [GB] United Kingdom ............. 9422260
Sep. 19, 1995 [GB] United Kingdom ............. 9519161

[51] Int. Cl.[6] .................................................. A61B 17/14
[52] U.S. Cl. ............................ 606/181; 606/182; 606/183
[58] Field of Search .................................... 606/181, 182, 606/183, 188, 185; 128/770, 765; 604/57, 52, 156, 272

[56] References Cited

U.S. PATENT DOCUMENTS 3,221,739  12/1965  Rosenthal .................. 606/181
4,653,513   3/1987  Dombrowski .............. 606/182

FOREIGN PATENT DOCUMENTS 0061102  9/1982  European Pat. Off. .
0427406  5/1991  European Pat. Off. .

*Primary Examiner*—Michael Powell Buiz
*Assistant Examiner*—Kevin Truong
*Attorney, Agent, or Firm*—Young & Thompson

[57] ABSTRACT

A skin pricker has a barrel (1) housing a lancet (3) which is urged rearwardly by a spring (4). A plunger (2) can move the lancet (3) against the spring (4) to project the lancet's needle tip or tips (18) from the forward end of the barrel (1). The plunger (2) presses on the rear of the lancet (3) through a firing pin (16) integrally formed with the plunger and connected to it by a thin web (17). Increased pressure after needle tip projection shears the web and the lancet (3) is free to be returned by the spring (4), withdrawing the needle tip or tips.

10 Claims, 2 Drawing Sheets

NEEDLE DEVICES FOR MEDICAL USE

BACKGROUND OF THE INVENTION

This invention relates to needle devices for medical use. It was developed primarily for skin prickers and will be described mainly in those terms. However, it could be applicable to injection devices.

Skin prickers are used for various medical purposes, one being to draw a drop of blood for analysis. Usually, that just requires a lancet with a single needle. But there is a tuberculin test, known as the Heaf Test, where a number of needles are driven into the skin, which is previously smeared with a substance that is carried by the needles into the blood vessels below the skin. The subsequent reaction is an indication of whether the test is positive or negative.

For this test it is necessary to ensure that the force of application of the needle lies within an upper and lower limit to maintain the reliability of the test.

DESCRIPTION OF THE PRIOR ART

Existing devices rely on driving needles into the skin against a biassing spring, or by storing up energy before overcoming a resistance, rather in the form of an impact punch.

While these methods can ensure that the needles will be pushed into the skin at above a known force, they rely on the skill of the operator not to push too hard and over reach the upper force limit.

Most prickers are throw-away items, but suffer from the disadvantage that, after use, the needle points are exposed leading to the possibility of accidental needle stick injury.

These days, with AIDS and hepatitis, there is wide spread concern surrounding the use of needles and their part in transmitting disease. Once a needle has been used on an infected person, subsequent use or an accidental prick could be fatal.

It is an aim of this invention to provide a simple and safe disposable pricker particularly suited to the Heaf Test. Although developed for that purpose, it should also prove suitable for carrying out certain vaccinations.

SUMMARY OF THE INVENTION

According to the present invention there is provided a needle device comprising a body with a needle at its forward end for skin penetration and an actuating member for exerting pressure on the body from the rearward end in the needle direction, the actuating member having a coupling to the body which includes a connection shearable by pressure above a predetermined limit thereby to render the device non-re-usable.

The device may be a skin pricker comprising a barrel-like housing with one end closed apart from at least one aperture, a lancet guided within the housing with a needle aligned with the or each aperture, spring means biasing the lancet away from the closed end, and a plunger guided by the other end of the housing and coupled to the lancet via a thin web, the plunger when pressed causing the lancet, in a first stage, to move to a limit against the spring means and the needle or needles to project from the housing, and causing in a second stage, with increased pressure, the thin web to shear and thereby release the lancet and allow the spring means to retract the lancet.

In the preferred form, for the Heaf Test, the lancet will be a multi-needle element, and conveniently the needles will be arranged in a circular array. The lancet body may then be generally cylindrical and guided on a central pin projecting inwardly from the closed end of the housing. The spring means is preferably a coil spring surrounding this pin and reacting against the closed end. The lancet will co-operate with the housing so that it will not twist, and therefore the needles will be kept aligned with the apertures.

Conveniently, the plunger couples to the lancet by a firing pin which, when the web has been sheared, falls away from both plunger and lancet. In the preferred form, the web connects the plunger and the firing pin, but the alternative of the web connecting the lancet and firing pin could be adopted. It would also be possible to omit the firing pin and connect the plunger and lancet directly by a shearable web.

BRIEF DESCRIPTION OF THE DRAWINGS

For a better understanding of the invention, one embodiment will now be described, by way of example, with reference to the accompanying drawings, in which.

DESCRIPTION OF THE PREFERRED EMBODIMENT

Figure 1:
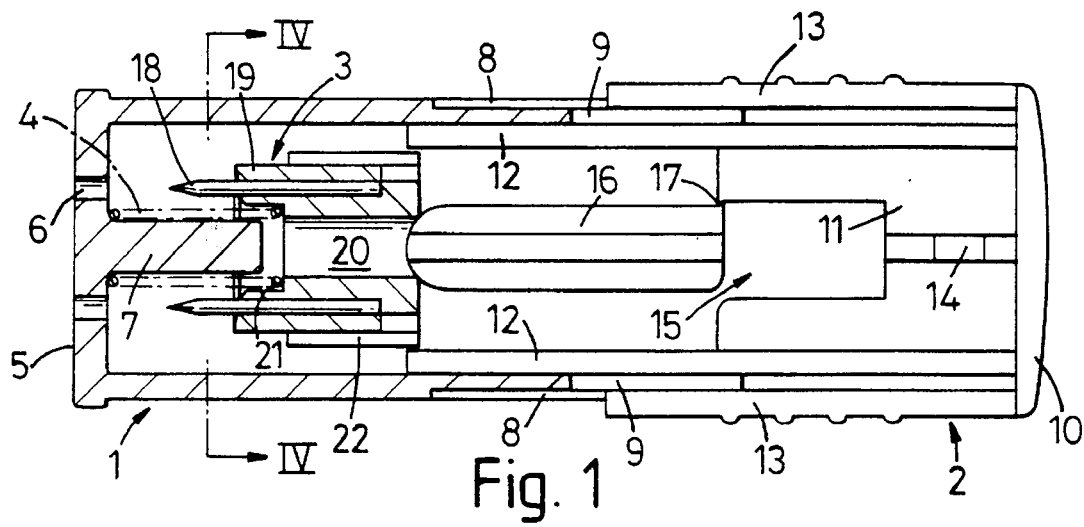
FIG. 1 is an axial section of a skin pricker ready to operate.

The pricker has four components, namely a barrel 1, a plunger 2, a multi-needle lancet 3 and a coil spring 4. The barrel 1 is of moulded plastics material and has a substantially closed forward end 5 pierced by a circular array of apertures 6. Within the barrel, a pin 7 projects rearwardly from the centre of this closed end 5 and is surrounded by the coil spring 4. From about its mid-length to the rear, open end, the barrel 1 has two elongate shallow, diametrically opposed recesses 8 in its outer surface, and centrally of these from about their mid-length to the free end there are slots 9.

The plunger 2 is also of moulded plastics material and has a thumb or finger pad 10 at its rear end transverse to a web 11 in the plane of the slots 9. At each longitudinal edge of this web there are two parallel fingers 12 and 13, the inner finger 12 being substantially longer and sliding down inside the barrel 1. The outer finger 13 is shaped to fit the associated recess 8, while the marginal portions of the web 11 enter the slots 9. Centrally, there are reinforcing ribs 14 on each side of the web between that and the pad 10. Beyond these from the pad 10, the web has a rectangular cut out 15 at whose mouth a firing pin 16 is connected to one corner by a thin web 17. The pin 16 is of cruciform section, with a rounded nose, and initially it lies coaxially within the barrel 1.

Figure 4:
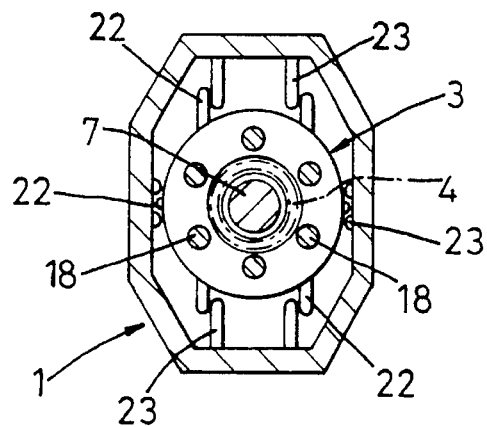
FIG. 4 is a cross section of the pricker on the line IV—IV of FIG. 1.
Figure 5:
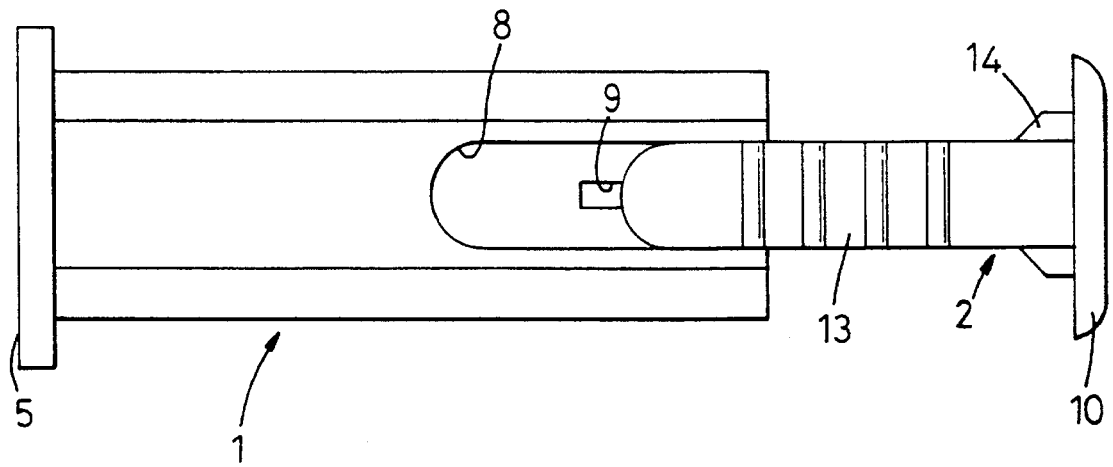
FIG. 5 is a side view of the pricker.

The lancet 3 is of generally cylindrical form with an annular array of needles 18 embedded in a plastics body 19, its central passage 20 being sized freely to receive the pin 7. But at the forward end this passage is enlarged to provide a shoulder 21 against which the spring 4 bears. The nose of the firing pin 16 seats in the rear end of the passage 20. Externally, the lancet body 19 has ribs 22 which co-operate with internal guide ribs 23 (FIG. 4) formed on the inside of the barrel 1, which help guide the lancet and prevent it rotating. The needles 18 are of course aligned with the apertures 6.

Figure 2:
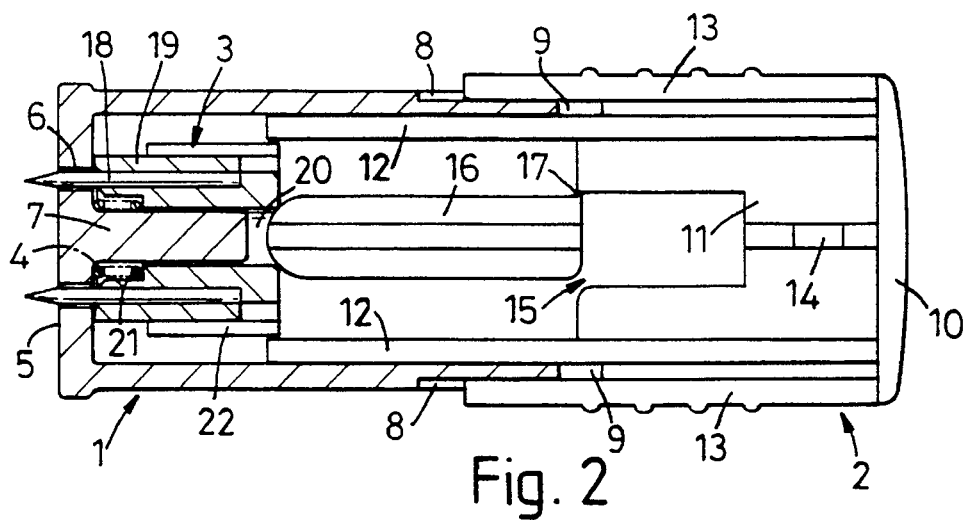
FIG. 2 is a section similar to FIG. 1, but with the pricker at the point of operation.
Figure 3:
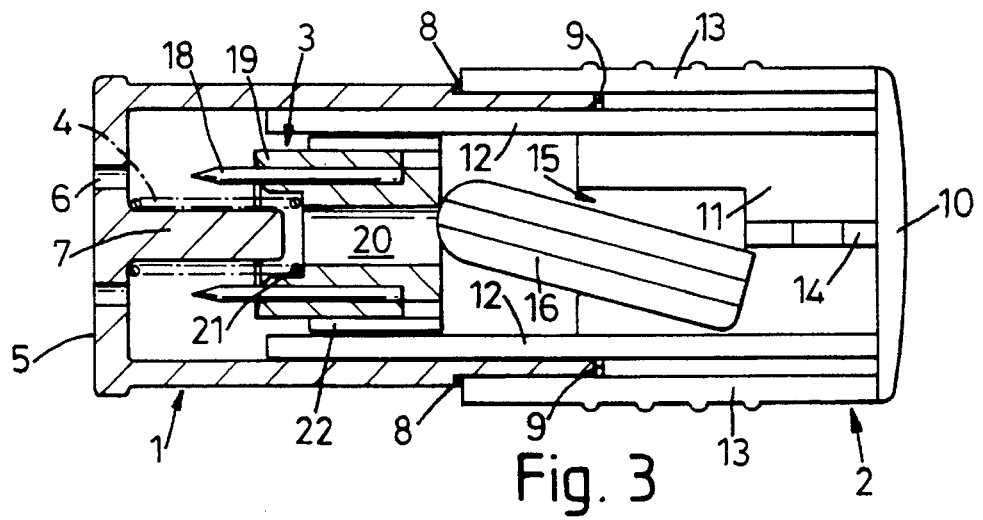
FIG. 3 is another similar section of the pricker, but after operation.

Before firing, the device is in the condition shown in FIG. 1. For use, the closed end 5 is placed against the skin and the plunger 2 is pressed. The pin 16 carries the lancet forward and projects the needles 18. This position is shown in FIG. 2. The operator then continues to press, which ensures that the needles 18 really do penetrate the skin. But the web 17 is weak, and at a certain predetermined controlled pressure it fractures. The pin 16 therefore falls away and the spring 4 exerts itself and retracts the lancet 3. The out-of-use position of FIG. 3 is thus achieved. Further pressure on the plunger cannot result in the needles being forced further into the skin as they are safely retracted. With the pin 16 broken away, the device is no longer useful and is discarded with the needles safely inside the barrel.

In the embodiment described, the firing pin 16 is connected to the plunger 2 by a shearable web 17. The arrangement could be reversed, with the firing pin 16 connected to the lancet by such a web, and the plunger being independent. The lancet might be lengthened and the pin shortened and narrowed so that the pin after shearing could enter the passage 20.

It would even be possible to dispense with the firing pin and make the plunger and lancet integral, with a shearable web joining the two parts. These would have to be configured so that, after the web fractures, the plunger does not interfere with the return movement of the lancet.

It may be possible to extend this principle to injection devices with hollow needles. For example a syringe could have a two-part plunger comprising a hollow piston joined to an actuating rod by a shearable web. When the piston reaches the end of its stroke continued pressure on the rod breaks the web allowing the rod freely to enter the arrested piston. The piston is therefore not retractable and the device is usable only once.

We claim:

1. A needle device comprising a body with a needle at its forward end for skin penetration and an actuating member for exerting pressure on the body from the rearward end in the needle direction, the actuating member having a coupling to the body which includes a connection that fractures under pressure above a predetermined limit thereby to render the device non-re-usable.

2. A device as claimed in claim 1, wherein the device is a skin pricker comprising a barrel-like housing with one end closed apart from at least one aperture, a lancet guided within the housing with a needle aligned with at least one aperture, spring means biasing the lancet away from the closed end, and a plunger guided by the other end of the housing and coupled to the lancet via a thin web, the plunger when pressed causing the lancet, in a first stage, to move to a limit against the spring means and at least one needle to project from the housing, and causing in a second stage, with increased pressure, the thin web to fracture and thereby release the lancet and allow the spring means to retract the lancet.

3. A device as claimed in claim 2, wherein the lancet has a plurality of needles.

4. A device as claimed in claim 3, wherein the needles are arranged in a circular array.

5. A device as claimed in claim 4, wherein the lancet body is generally cylindrical and is guided on a central pin projecting inwardly from the closed end of the housing.

6. A device as claimed in claim 5, wherein the spring means is a coil spring surrounding the pin and reacting against the closed end.

7. A device as claimed in claim 3, wherein the lancet co-operates with the housing so that it will not twist, thereby keeping the needles aligned with the apertures.

8. A device as claimed in claim 2, wherein the plunger couples to the lancet by a firing pin which, when the web has been fractured, falls away from both plunger and lancet.

9. A device as claimed in claim 8, wherein the web connects the plunger and firing pin.

10. A device as claimed in claim 8, wherein the web connects the lancet and firing pin.

* * * * *